US006007507A

United States Patent [19]

Ledany

[11] Patent Number: 6,007,507

[45] Date of Patent: Dec. 28, 1999

[54] BODY STRETCHING AND DECOMPRESSION SYSTEM

[76] Inventor: Ori Ledany, 1550 Sandpebble Dr., Wheeling, Ill. 60090

[21] Appl. No.: 09/082,954

[22] Filed: May 21, 1998

[51] Int. Cl.[6] .......................... A61F 5/00

[52] U.S. Cl. .......................... 602/32; 602/36

[58] Field of Search .......................... 602/32–40; 606/237–238

[56] References Cited

U.S. PATENT DOCUMENTS

| | | | |
|---|---|---|---|
| 885,243 | 4/1908 | Haas | 602/34 |
| 3,699,953 | 10/1972 | Mason | 602/34 |
| 4,608,971 | 9/1986 | Borschneck | 602/38 |
| 5,010,880 | 4/1991 | Lamb | 602/36 |

*Primary Examiner*—Michael A. Brown

*Attorney, Agent, or Firm*—Welsh & Katz, Ltd.

[57] ABSTRACT

A body stretching and decompression system for use on a horizontal surface is disclosed. The system includes a frame having first and second portions adjustably connected together. A pair of hand grips are secured to the second portion of the frame. The system also includes a cuff assembly to be secured to a user, a rollable positioning member for allowing a user to move on the horizontal surface in a direction away from the first portion of the frame, and a resilient coupling resiliently attaching the first portion of said frame to the cuff assembly. When the cuff assembly is secured to a user and the user is disposed on the positioning member in an initial position with respect to the first portion of the frame, the user may apply a user-selected amount of traction to the user's skeletal system by grasping the hand grips and moving the user's body to an extended position. The amount of traction is generally proportional to the distance between the initial and extended positions.

10 Claims, 3 Drawing Sheets

BODY STRETCHING AND DECOMPRESSION SYSTEM

FIELD OF THE INVENTION

The present invention generally relates to therapeutic devices for providing traction to a patient's skeletal system and, more particularly, to a body stretching and decompression system which allows a patient to apply a desired amount of traction on the patient's skeletal system when the patient is disposed in a horizontal, prone position.

BACKGROUND OF THE INVENTION

Medical personnel have used spinal traction therapy to treat various back conditions such as, for example, spinal instability, degenerative disc disease, spinal stenosis, lumbrosacral sprain or strain, chronic sciatica, disc herniation, spondylolisthesis, lumbar osteoarthritis, and facet pathology. Spinal traction therapy can be provided by two general classes of devices as discussed in greater detail hereafter.

Gravity inversion therapy involves suspending a user in a head-down position so that the user's own body weight provides the necessary traction force due to the force of gravity. In one type of gravity inversion device, a pair of hinged, padded cylinders are secured around a user's ankles so that the user's body weight decompresses the ankles, knees, and spinal cord. A second type of gravity inversion device utilizes an adjustable footboard and a horizontal bar which, when the user is disposed in an inverted position, is placed above the lower portion of a user's hips so that the weight of the user's torso decompresses the user's spine.

Gravity inversion therapy devices suffer from a number of disadvantages. For example, not only are users typically afraid to be hung upside down, but also users may have feelings of disorientation and dizziness both during and after the gravity inversion therapy. Further, blood rushing to the head during use of a gravity inversion device causes pressure on the eyes and sinuses and increases the risk of popping a blood vessel or stroke, especially when the user has high blood pressure. Additionally, gravity inversion devices are difficult to use for those who are not particularly athletically talented.

Therapeutic tables have been utilized for providing traction to a user's lumbar region when the user is disposed in a horizontal, prone position. One such device includes a frame and a table top. The table top includes an upper-body section rigid with respect to the frame and a lower-body section slideable with respect to the frame. A pair of hand grips on the upper-body section are accessible by a user with the user's arms above the head to anchor the upper body. A pelvic belt anchor is attached to the lower-body section of the table top. A cylinder and piston assembly moves the lower-body section of the table top to cyclically increase and decrease the distance between the hand grips and the pelvic belt anchor. This action cyclically applies traction to the lumbar region of the user's spine. While these devices are satisfactory for their intended uses, they are quite expensive to manufacture and maintain and do not allow a user to actively control the amount of traction applied. Additionally, they cannot be easily adapted for portability.

SUMMARY OF THE INVENTION

It is desirable to provide a body stretching and decompression system that allows a user to apply a user-selected amount of traction to the user's skeletal system and includes a cuff assembly that is attached to, for example, the user's legs and is resiliently attached to the stationary portion of a frame. A user may apply varying amounts of traction by moving the user's body from an initial, at-rest position to a number of extended positions which are varying distances in a horizontal direction away from the stationary portion of the frame. The amount of traction is related to the amount of movement of the user's body and may be directly proportional to such movement. Such a system has a number of advantages.

First, the use of such a system does not involve the health risks and difficulties of use associated with the gravity inversion traction therapy devices discussed above. Second, the costs of manufacturing and maintaining such a system are significantly and dramatically lower than the cost of manufacturing and maintaining a therapeutic table as, for example, discussed above. Third, patient compliance with a prescribed traction therapy regimen is increased due, for example, to the ease with which a patient uses and assembles such a system. Fourth, such a system is most amenable for home use because, for example, it may be portable and easy for a user to assemble and use.

Other features and advantages of the invention will become apparent from the description that follows.

DETAILED DESCRIPTION OF THE INVENTION

Figure 1:
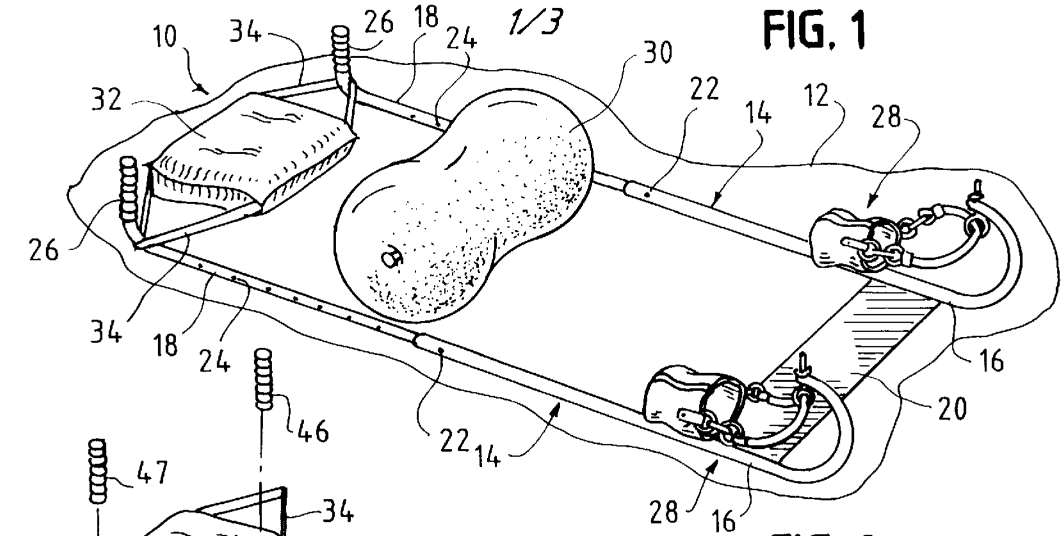
FIG. 1 is a perspective view of a body stretching and decompression device according to an embodiment of the present invention.

Referring to FIG. 1, a perspective view of an embodiment of a body stretching and decompression system 10 for use on a horizontal surface 12 is shown. System 10 includes a frame member 14 having two first, stationary portions 16 and two second, moveable portions 18 which are adjustably connected together. The first portions 16 of the frame 14, which are secured together by means of support member 20, both include a resilient pin 22 which engages a plurality of holes 24 in the second portion 18 corresponding thereto.

First and second hand grips 26 are mounted on the distal end of the second portions 18 of frame 14. Hand grips 26 can be attached in a number of positions with respect to the first portions 16 due to the cooperation of resilient pins with the holes 24. System 10 includes two cuff assemblies 28 and a rollable positioning member 30 located on horizontal surface 12 between the first and second portions 1 and 18 of the frame 14. Preferably, positioning member 30 comprises an inflatable, rubber or plastic ball which may have a cylindrical or "peanut" shape. Users of varying height may apply a user-selected amount of traction to their skeletal system by engaging pins 22 with selected ones of holes 24, securing cuff assemblies 28 to their ankles, lying in a horizontal, prone position on the positioning member 30 at an initial, at-rest location on the horizontal surface 12, and moving their bodies to an extended position as discussed in greater detail hereafter.

Figure 2:
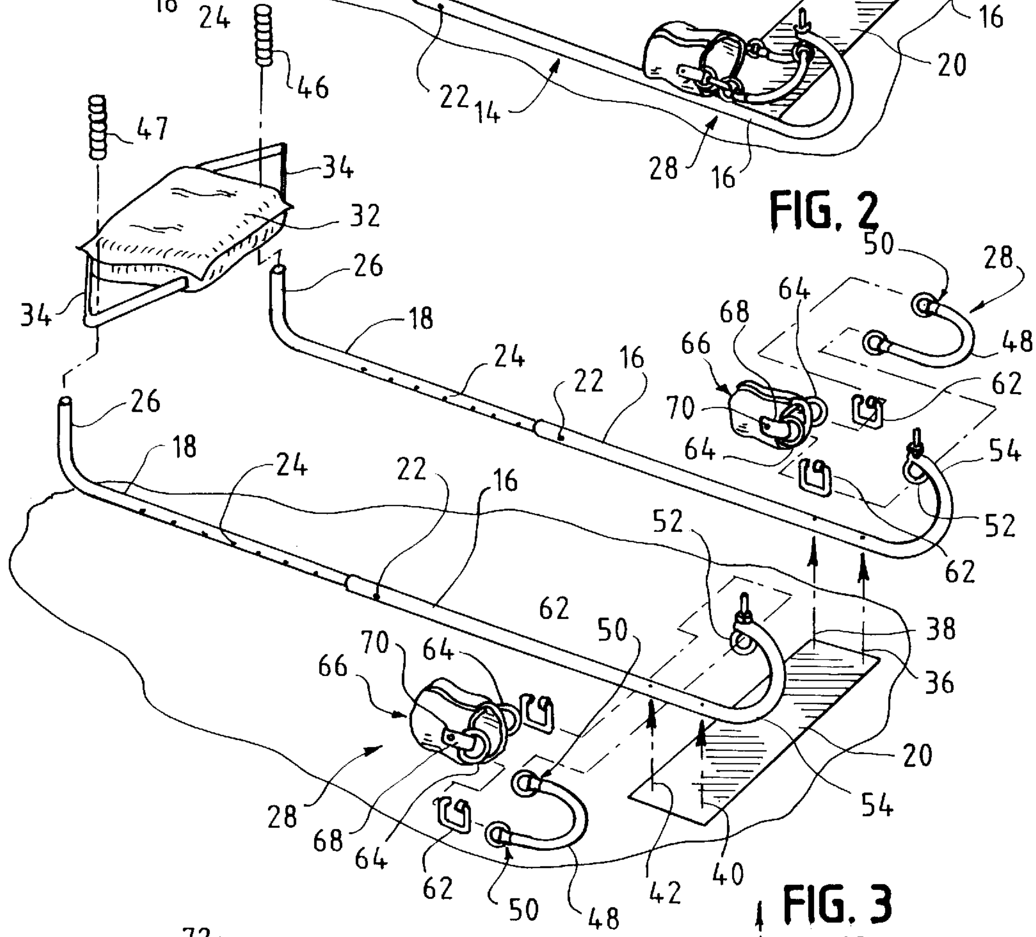
FIG. 2 is an exploded view of the body stretching and decompression device shown in FIG. 1.

Referring to FIG. 2, an exploded view of the body stretching and decompression system 10 is shown. System 10 also includes a pillow 32 upon which a user may lay their head, if desired, during use of the system 10. Pillow 32 includes elastic straps 34 so that it will be positioned on horizontal surface 12 generally between hand grips 26. Support member 20 is secured to the first portions 16 of the frame 14 via pins 36, 38, 40, and 42 as shown. Padded handle cylinders 44 and 46 are mounted on hand grips 26 as shown for the comfort of a user of the system 10.

Figure 3:
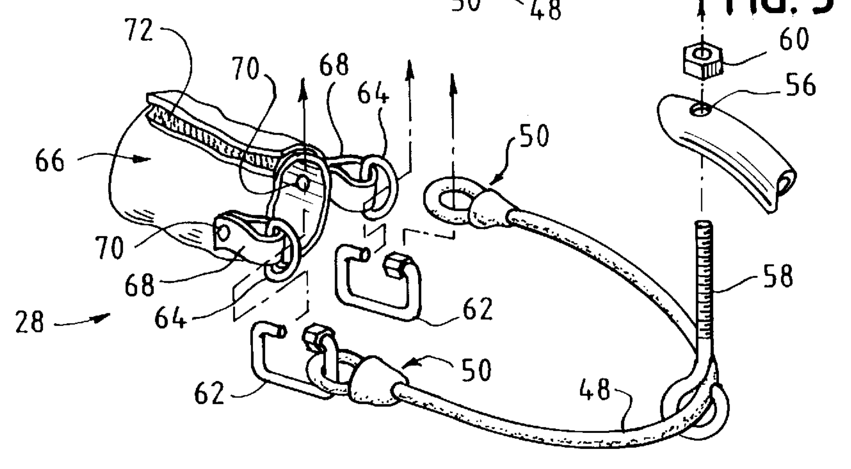
FIG. 3 is an enlarged view of a portion of the body stretching and decompression device shown in FIG. 2.

Referring to FIGS. 2 and 3, cuff assemblies 28 both include a resilient tube 48 having a loop fastener 50 disposed at both ends thereof. The body of resilient tubes 48 pass through the eye connector 52 which is secured to the raised portions 54 of the first portions 16 of the frame 14 via aperture 56, threads 58 and nut 60 as best shown in FIG. 3. A C-clamp 62 removably couples all of the loop fasteners 50 to a corresponding D-ring 64. Each pair of D-rings 64 are secured to a removable cuff 66 by a folded strap 68 and snap connector 70. It should be appreciated that the resilient tube can be connected to the cuff at two locations in any suitable manner. Cuffs 66 comprise a rectangular sheet of a suitable material such as, for example, leather that is folded over on itself and secured together as shown via hook and loop fasteners 72.

Figure 4A:
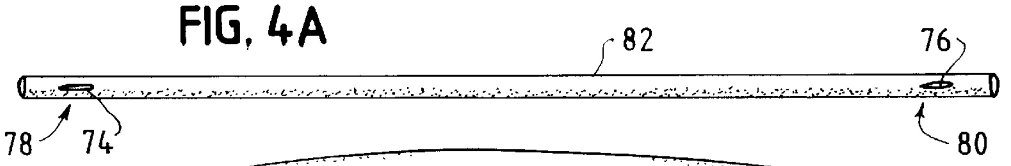
FIGS. 4A–4F are a series of elevational views which illustrate a method by which the loop attachments on both ends of the resilient tube shown in FIGS. 1–3 are formed.
Figure 4B:
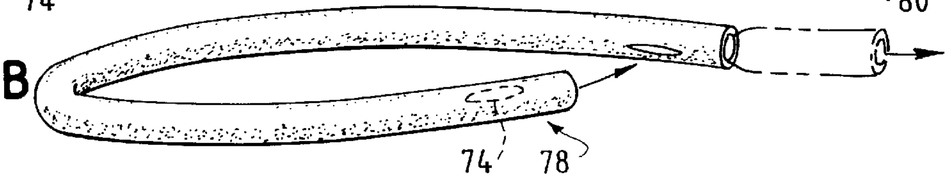
Figure 4C:
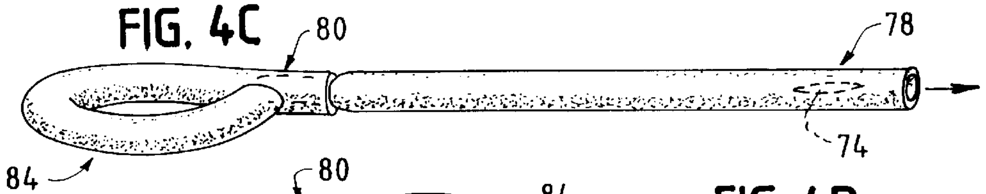
Figure 4D:
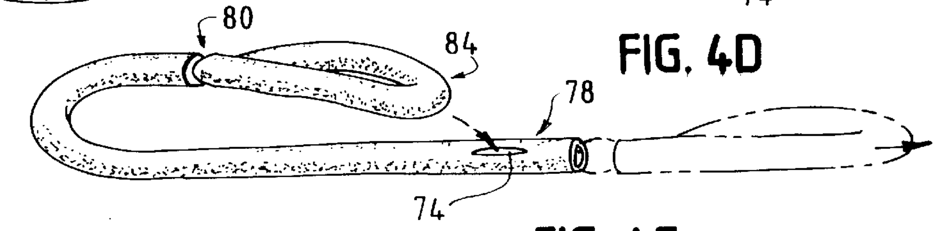
Figure 4E:
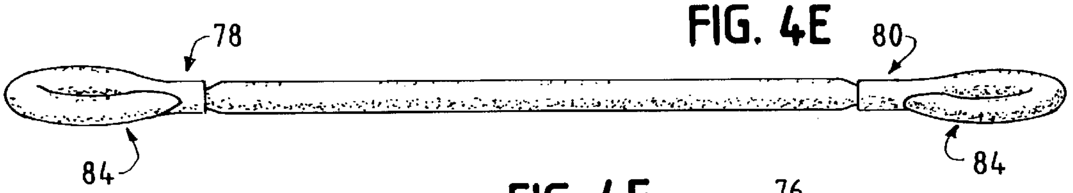
Figure 4F:
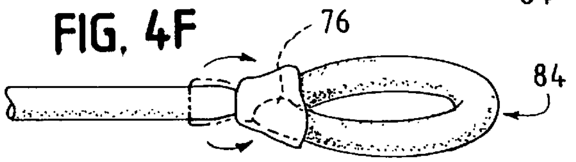

FIGS. 4A–4F are a series of elevational views which illustrate a method by which the loop fasteners 50 are integrally formed as a portion of and are located at both ends of the resilient tubes 48 shown in FIGS. 1–3. To form a loop fastener 50, longitudinal slits 74 and 76 are formed in ends 78 and 80 of the tube 82 as shown in FIG. 4A. Next, the end 78 of tube 82 is inserted through the slit 76 and pulled therethrough as shown in FIG. 4B. Referring to FIG. 4C, the end 80 of the tube 82 is moved down the length of the tube 80 to the position shown to form a lasso connector 84. A second lasso connector 86 is formed by inserting lasso connector 84 through the slit 74 and pulling the same to the position shown in FIG. 4D. The lasso connector is synched and tightened (not shown) about any member to which it is connected. Further, an end of the resilient tube 82 is folded over onto itself to cover the corresponding slit, if desired, as shown in FIG. 4F.

Figure 5:
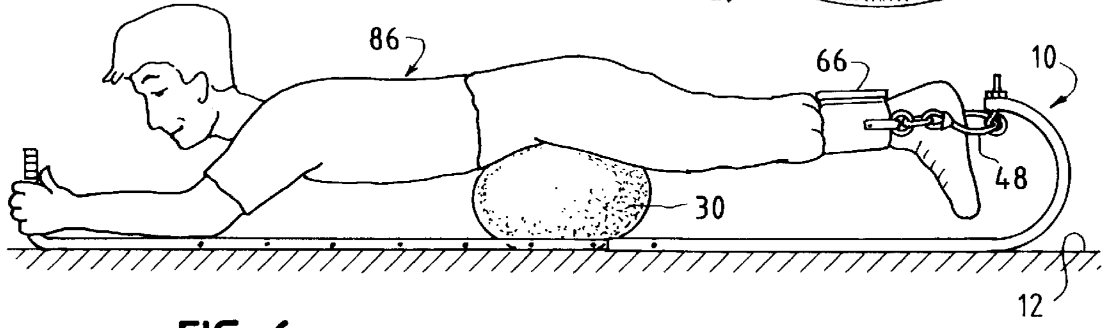
FIG. 5 is a side view of the body stretching and decompression system shown in FIG. 1 in which a user is disposed in an initial, at-rest position wherein no traction is applied to the user's skeletal system.

Referring to FIG. 5, a side view of the body stretching and decompression system 10 is shown in which a user 86 is disposed in an initial, at-rest position on the positioning member 30 and horizontal surface 12. Cuff 66 is attached to and around the ankles of the user 86. In this position, no traction is applied to the user's skeletal system because there is no tension or load applied to the resilient tube 48. Movement from this position applies tension to the tube 48 and, therefore, traction to the user's skeletal system. It is contemplated by the present invention that cuff 66 may be secured to the user's shins, knees or thighs so that differing portions of the user's skeletal system can be stretched and decompressed. Further, it is contemplated by the present invention that the cuff 66 may comprise a girdle worn by the user so that the user 86 may stretch and decompress only the user's spine. The term "cuff" as used herein is intended to include generally any form of device for attaching the resilient tubes to any part or portion of the user's body, regardless of whether such attachment device is a cylindrical cuff, corset, girdle, halter, sheath, or the like.

Figure 6:
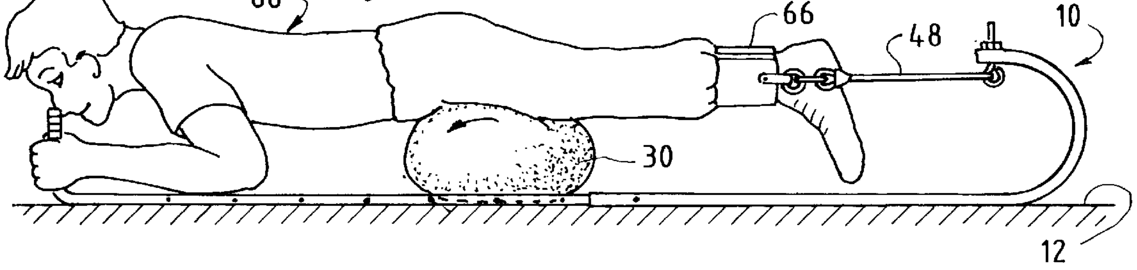
FIG. 6 is a side view of the body stretching and decompression system shown in FIG. 1 in which the user is disposed in an extended position wherein a user selected amount of traction is applied to the user's skeletal system.

FIG. 6 is a side view of the body stretching and decompression system 10 shown in FIG. 1 in which the user is disposed in an extended position wherein a user-selected amount of traction is applied to the user's skeletal system. The amount of traction applied to the user's skeletal system is directly proportional to the distance that the user 86 moves in a direction parallel to the horizontal surface 12 from the initial position to a user-selected extended position. Because the user 86 acts against the force applied to the user's skeletal system by cuff and resilient tube 48 by pulling on hand grips 26, use of the system 10 is particularly suited for physical therapy or other applications where it is desirable to increase the strength of the user's biceps and upper chest area.

Figure 7:
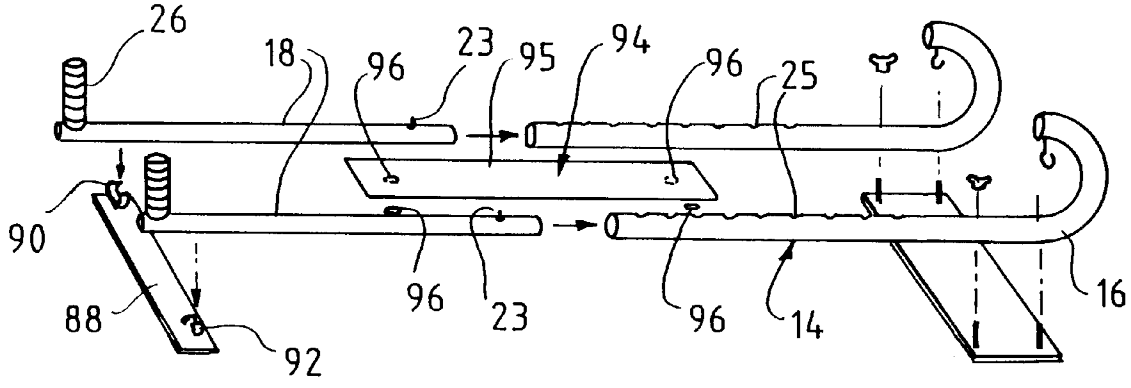
FIG. 7 is a partial, exploded view of the body stretching and decompression system shown in FIG. 1 which shows a support clip bar.

FIG. 7 is a partial, exploded view of the body stretching and decompression system shown in FIG. I which illustrates a support clip bar 88. Bar 88 includes two resilient clips 90 and 92 which are attached to the second portions 18 of frame 14 to stabilize the second portions 18 with respect to each other during use. Both clips 90 and 92 are rotatable so that the bar 88 can be clipped to one of the second portions 18 when the unit is stored.

A wheeled positioning member 94 having four wheels 96 is mounted on a generally planar support member 95. Member 95 includes an ergonomically designed pad (not shown) which is designed to fit a portion of a user's body to accommodate a user's health status and other special needs. Member 94 allows a user to supply a user-selected amount of traction to the user's skeletal system as discussed above.

FIG. 7 shows an alternate, preferred way to allow the position of handles 26 to be adjusted. In this case, a resilient pin 23 is placed on each one of the second portions 18 and a plurality of corresponding holes 25 are placed on the first portions 16 of frame 14.

While the invention has been illustrated and described in detail in the drawings and foregoing description, the same is considered as illustrative and not restrictive in character, it being understood that all changes and modification that come within the spirit of the invention are desired to be protected.

I claim:

1. A body stretching and decompression system for use on a horizontal surface, comprising:

a frame having first and section portions, a pair of hand grips being secured to the second portion of said frame;

a cuff assembly to be secured to a user;

a positioning member for allowing a user to move parallel to the horizontal surface in a first direction away from the first portion of said frame; and a resilient coupling resiliently attaching the first portion of said frame to said cuff so that when said cuff is secured to a user and the user is disposed on said positioning member in an initial position with respect to the first portion of said frame, the user may apply a user-selected amount of traction to the user's skeletal system by grasping said hand grips and moving the user's body away from the first portion of said frame to an extended position, the amount of traction applied being related to the distance between the initial and extended positions.

2. The body stretching and decompression system of claim 1 wherein the second portion of said frame is moveable with respect to the first portion of said frame, said frame further comprising means for securing the second portion of said frame to the first portion of said frame in a plurality of positions on the horizontal surface.

3. The body stretching and decompression system of claim 1 wherein said cuff assembly comprises first and second cuffs that are to be secured to the legs of the user to allow the user's spine, knees and ankles to be decompressed.

4. The body stretching and decompression system of claim 1 wherein said cuff assembly includes first and second connectors and wherein said resilient coupling includes a resilient tube, the ends of said tube being connected to said first and second connectors by a corresponding loop fastener.

5. The body stretching and decompression system of claim 4 wherein both of said loop fasteners are integrally formed as a portion of said tube by a method including the steps of forming a longitudinal slit in a first end of said tube, inserting the second end of said tube through said slit, and pulling the second end of said tube out the first end of said tube to form a lasso, inserting said connector through said lasso, and synching said lasso.

6. The body stretching and decompression system of claim 1 wherein said positioning member comprises an elongated inflatable ball.

7. The body stretching and decompression system of claim 6 wherein said elongated inflatable ball has a "peanut" shape.

8. The body stretching and decompression system of claim 1 wherein the amount of traction applied to the user's body is proportional to the distance between the initial and extended positions with respect to said first portion of said frame.

9. The body stretching and decompression system of claim 1 further comprising a stabilizing member attached to the second position of said frame.

10. The body stretching and decompression system of claim 1 wherein said positioning member comprises a support member having at least two wheels.

* * * * *